(12) United States Patent
Kadam et al.

(10) Patent No.: US 10,865,180 B2
(45) Date of Patent: Dec. 15, 2020

(54) PROCESS FOR THE PREPARATION OF L-NOREPINEPHRINE BITARTRATE MONOHYDRATE HAVING HIGH ENANTIOMERIC PURITY

(71) Applicant: HARMAN FINOCHEM LIMITED, Mumbai (IN)

(72) Inventors: Vijay Trimbak Kadam, Aurangabad (IN); Nareesh Saranapu, Ramachandrapuram (IN); Amin Rashid Shaikh, Ahmednagar (IN); Harpreet Singh Minhas, Mumbai (IN); Gurpreet Singh Minhas, Mumbai (IN)

(73) Assignee: HARMAN FINOCHEM LIMITED, Mumbai (IN)

( * ) Notice: Subject to any disclaimer, the term of this patent is extended or adjusted under 35 U.S.C. 154(b) by 0 days.

(21) Appl. No.: 16/537,324

(22) Filed: Aug. 9, 2019

(65) Prior Publication Data

US 2020/0048185 A1 Feb. 13, 2020

(51) Int. Cl.
*C07C 213/04* (2006.01)

(52) U.S. Cl.
CPC .................. *C07C 213/04* (2013.01)

(58) Field of Classification Search
CPC .................................................. C07C 213/04
See application file for complete search history.

(56) References Cited

U.S. PATENT DOCUMENTS 2,786,871 A 3/1957 Winterhalder et al.

FOREIGN PATENT DOCUMENTS

| CN | 101798271 A | 8/2010 |
| CN | 107298646 A | 10/2017 |
| WO | 2009/004593 A2 | 1/2009 |
| WO | 2013/008247 A1 | 1/2013 |
| WO | 2016/038422 A1 | 3/2016 |

OTHER PUBLICATIONS

Fodor, et al., "A New Synthesis of DL-NOR-Adrenaline and of Related Amino Alcohols with a Primary Amino Group", Acta Chimica Academiae Scientiarum Hungaricae (1951) 1, 395-402.
Simonoff, et al., "Amino Alcohols. XVII. Arylethanolamines", Journal of the American Pharmaceutical Association, 1946, 35, 306-309.
Tullar, "The Resolution of dl-Arterenol", J. Am. Chem. Soc., 1948, 70(6), pp. 2067-2068.

*Primary Examiner* — Brenda L Coleman
(74) *Attorney, Agent, or Firm* — Kramer Amado, P.C.

(57) ABSTRACT

The present invention, discloses optically pure compounds of l-Norepinephrine and its acid addition salts and hydrates and process for the preparation thereof. Specifically, the present invention discloses optically pure compounds of l-Norepinephrine bitartrate, its process of preparation and pharmaceutical compositions comprising the same.

9 Claims, No Drawings

PROCESS FOR THE PREPARATION OF L-NOREPINEPHRINE BITARTRATE MONOHYDRATE HAVING HIGH ENANTIOMERIC PURITY

TECHNICAL FIELD

The present invention, in general, relates to highly optically pure compounds of l-Norepinephrine and its acid addition salts and hydrates and to its process for the preparation. Specifically, the present invention relates to optically pure compounds of l-Norepinephrine bitartrate, its process of preparation and pharmaceutical compositions comprising the same.

BACKGROUND

Norepinephrine Bitartrate (Arterenol Bitartrate) is chemically known as (−)-α-(aminomethyl)-3, 4-dihydroxybenzyl alcohol tartrate (1:1) (salt) monohydrate is a catecholamine family that functions in the brain and body as a hormone and neurotransmitter. As a stress hormone, Norepinephrine affects parts of the brain where attention and responding actions are controlled. Along with epinephrine, Norepinephrine also underlies the fight-or-flight response, directly increasing heart rate, triggering the release of glucose from energy stores, and increasing blood flow to skeletal muscle. Norepinephrine also has a neurotransmitter role when released diffusely in the brain as an anti-inflammatory agent.

LEVOPHED® (l-Norepinephrine) is supplied in sterile aqueous solution in the form of the bitartrate salt to be administered by intravenous infusion following dilution. Norepinephrine is sparingly soluble in water, very slightly soluble in alcohol and ether, and readily soluble in acids. Each ml contains the equivalent of 1 mg base of Norepinephrine, sodium chloride for isotonicity, and not more than 2 mg of sodium metabisulfite as an antioxidant.

Norepinephrine Bitartrate is (−)-α-(amino methyl)-3,4-dihydroxybenzyl alcohol tartrate (1:1) (salt) monohydrate and has the following structural formula:

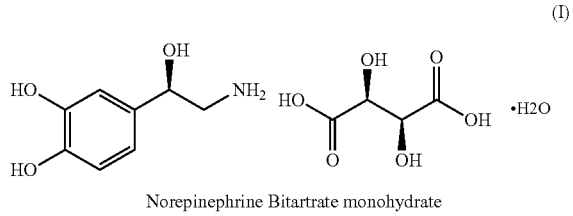 [SMILES: NC[C@H](O)c1ccc(O)c(O)c1 ; O=C(O)[C@@H](O)[C@H](O)C(=O)O]

Norepinephrine Bitartrate monohydrate (l)-Norepinephrine was first disclosed in 1947 by Sterling Drugs. U.S. Pat. No. 2,774,789 discloses the resolution of dl-Norepinephrine with optically active acids such as d-tartaric acid, l-malic acid or N-benzoyl-l-threonine. The patent does not disclose the basic synthesis of dl-Norepinephrine.

*Journal of the American Chemical Society*, Volume 70 (6), 1948 describes the resolution of dl-Norepinephrine in to d-arterenol-d-bitartrate and l-arterenol-d-bitartrate in water and aqueous methanol. Further it also describes isolation of d-arterenol and l-arterenol form above tartrate salts.

U.S. Pat. No. 2,786,871 discloses the process for the preparation of arterenol wherein chloroacetopyrocatechol is treated with ammonia and arterenol is obtained in 50% yield.

*J. Am. Pharm. Association* (1946) 35, 306-309 discloses preparation of 3,4-dihydroxyaminoacetophenone by reacting 3,4-dihydroxy-α-chloroacetophenone with dibenzyl amine, followed by hydrogenation of the resulting dibenzylamino ketone. The main disadvantage of this reaction is the formation of derivatives of dibenzyl amines, which carried over to final product in the form of impurities.

*Acta Chimica Academiae Scientiarum Hungaricae* (1951), 1, 395-402 discloses preparation of 3, 4-dihydroxy-α-aminoacetophenone from 3,4-dihydroxyphenyloxo acetaldehyde and benzyl amine followed by reduction of the benzylamino ketone intermediate. The main disadvantage of this method is that the starting acetaldehyde derivative is very expensive and not easily available.

CN101798271A describes reduction of 3,4-dihydroxy-α-aminoacetophenone hydrochloride in water as solvent followed by neutralization with aqueous ammonia. Since dl-Norepinephrine has partial solubility in aqueous basic medium, this process results in a loss of product. Also, it is necessary to maintain low volume of solvent throughout the process for better yields making the process stringent.

WO2009004593 describes the process for the preparation of Epinephrine wherein (−) epinephrine is obtained by chiral separation of dl-epinephrine using the chiral acid such as L-tartaric acid with an optical purity of 95.24%.

WO2013008247 discloses a process for preparation of (dl)-norepinephrine hydrochloride salt by reacting 3,4-dihydroxy-a-haloacetophenone with hexamethylenetetramine to provide hexamine salt; followed by hydrolysis and hydrogenation. However, this process fails to teach the resolution of (dl)-norepinephrine hydrochloride and preparation of l-Norepinephrine Bitartrate monohydrate.

WO2016038422 discloses a process for the preparation of optically enriched adrenaline or adrenaline tartrate comprising the steps of: (a) reacting a mixture of (−)-adrenaline and (+)-adrenaline with L(+)-tartaric acid to form adrenaline tartrate; (b) contacting the adrenaline tartrate with less than 1 equivalent of ammonium hydroxide. However, the product achieved is with purity of only 98%.

CN107298646 describes the process for the preparation of Norepinephrine wherein L-Norepinephrine tartrate is obtained by chiral separation of dl-Norepinephrine using the chiral acid such as L-tartaric acid. The chiral separation step using L-tartaric acid is repeated once to obtain pure Norepinephrine. However, there is no information on bitartrate salt and its optical purity.

In light of the above, there remains a need in the art for highly pure l-Norepinephrine Bitartrate having high enantiomeric purity i.e. greater than 99.0% so as to provide enhanced therapeutic efficacy and safety when administered. Surprisingly the present inventors have found out a process for the preparation of (l)-Norepinephrine Bitartrate having enantiomeric purity greater than 99.5%, for which protection is sought.

OBJECT OF THE INVENTION

It is a primary object of the present invention to provide a process for preparation of l-Norepinephrine Bitartrate monohydrate of formula (I) having optical purity more than 99.0% enantiomeric excess.

It is another objective of present invention to provide optically pure compound of l-Norepinephrine Bitartrate having optical purity more than 99.0% enantiomeric excess and compositions comprising the same.

SUMMARY OF THE INVENTION

In line with the above objectives, the present invention provides optically pure compounds of l-Norepinephrine Bitartrate having optical purity of more than 99.5% enantiomeric excess.

In another aspect, the present invention provides a process for preparation of l-Norepinephrine Bitartrate monohydrate of formula (I) which process comprising;
a) Treating dl-Norepinephrine base with D-(−)-tartaric acid in water and an organic solvent to obtain crude l-Norepinephrine bitartrate;
b) converting the l-Norepinephrine bitartrate obtained in step (a) into l-Norepinephrine base by treating with ammonia;
c) treating the l-Norepinephrine base obtained in step (b) with D-(−)-tartaric acid to obtain pure l-Norepinephrine bitartrate;
d) converting the l-Norepinephrine tartrate obtained in step (c) into l-Norepinephrine base by treating with ammonia;
e) treating the l-Norepinephrine base obtained in step (d) with L-(+)-tartaric acid to obtain l-Norepinephrine Bitartrate having an optical purity greater than 99% enantiomeric excess and
f) purifying the l-Norepinephrine Bitartrate monohydrate from water/IPA mixture to obtain l-Norepinephrine Bitartrate monohydrate having high optical purity of greater than 99.5%.

In yet another aspect, the present invention provides pharmaceutical composition comprising l-Norepinephrine Bitartrate having optical purity greater than 99.0% enantiomeric excess, preferably, greater than 99.5% enantiomeric excess along with one or more pharmaceutical carriers/excipients.

In a further aspect, the invention provides a synthetic process for preparation of dl-Norepinephrine free base in high yield and chemical purity and its subsequent resolution to obtain l-Norepinephrine Bitartrate.

In yet another aspect, the invention provides a process for the preparation of highly pure l-Norepinephrine base in high yield and optical purity.

Various embodiments disclosed herein relate to a process for the preparation of optically pure l-Norepinephrine bitartrate monohydrate, by treating dl-Norepinephrine base with D-(−)-tartaric acid in the presence of water and an organic solvent to obtain crude l-Norepinephrine bitartrate; converting the l-Norepinephrine bitartrate obtained in step (a) into l-Norepinephrine base; and treating the l-Norepinephrine base obtained in step (b) with L-(+)-tartaric acid and water to obtain l-Norepinephrine Bitartrate monohydrate having an optical purity of greater than 99%. In various embodiments, the step of converting the l-Norepinephrine bitartrate into l-Norepinephrine base involves treating the bitartrate with ammonia. Various embodiments disclosed herein include an additional step of further purifying the l-Norepinephrine Bitartrate monohydrate having an optical purity of greater than 99% by crystallization from a water/IPA mixture to obtain l-Norepinephrine Bitartrate monohydrate having an optical purity of greater than 99.5%.

In various embodiments discloses herein, the process includes a step of converting l-Norepinephrine bitartrate into l-Norepinephrine base, by:
a first step of converting the l-Norepinephrine bitartrate obtained in step (a) into l-Norepinephrine base by treating with ammonia;
a second step of treating the l-Norepinephrine base obtained in the first step with D-(−)-tartaric acid to obtain pure l-Norepinephrine bitartrate; and
a third step of converting the l-Norepinephrine bitartrate obtained in the second step into l-Norepinephrine base by treating with aqueous ammonia solution.

Various embodiments disclosed herein relate to a process for the preparation of optically pure l-Norepinephrine bitartrate monohydrate, by:
treating dl-Norepinephrine base with D-(−)-tartaric acid to obtain crude l-Norepinephrine bitartrate, in the presence of water and an organic solvent selected from the group consisting of methanol, ethanol, isopropanol, n-butanol, acetonitrile, dioxane, dimethylformamide, dimethylsulphoxide, halogenated solvents, and mixtures thereof;
converting the l-Norepinephrine bitartrate into l-Norepinephrine base; and
treating the l-Norepinephrine base with L-(+)-tartaric acid and water to obtain l-Norepinephrine Bitartrate monohydrate having an optical purity of greater than 99%.

Various embodiments disclosed herein relate to a process for the preparation of optically pure l-Norepinephrine bitartrate monohydrate, by:
treating dl-Norepinephrine base with D-(−)-tartaric acid to obtain crude l-Norepinephrine bitartrate, in the presence of water and a halogenated solvent selected from the group consisting of dichloromethane, chloroform, and mixtures thereof;
converting the l-Norepinephrine bitartrate into l-Norepinephrine base; and
treating the l-Norepinephrine base with L-(+)-tartaric acid and water to obtain l-Norepinephrine Bitartrate monohydrate having an optical purity of greater than 99%.

Various embodiments disclosed herein relate to a process for the preparation of optically pure l-Norepinephrine bitartrate monohydrate from a dl-Norepinephrine base, wherein the dl-Norepinephrine base is prepared by:
reacting catechol with chloroacetyl chloride in the presence of a Lewis acid to obtain a compound of Formula II;

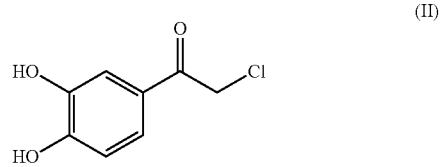 [SMILES: O=C(CCl)c1ccc(O)c(O)c1]

reacting the compound of Formula II with Hexamine to obtain a compound of Formula III;

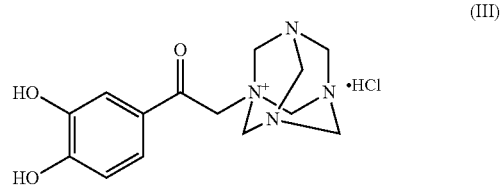 [SMILES: O=C(C[N+]12CN3CN(CN(C3)C1)C2)c1ccc(O)c(O)c1 ; Cl]

converting the compound of Formula III into the hydrochloride salt of a ketone of formula IV; and

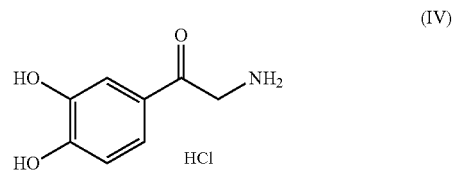

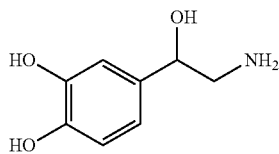

(V)

hydrogenating the ketone of formula (IV) to obtain dl-Norepinephrine of formula V.

Various embodiments disclosed herein relate to a pharmaceutical composition including l-Norepinephrine bitartrate monohydrate having an optical purity of more than 99.5%; and one or more pharmaceutically acceptable carrier(s).

DETAILED DESCRIPTION OF THE INVENTION

For the purpose of the present invention, optically pure compounds of the invention comprise l-Norepinephrine base, l-Norepinephrine tartrate salts and its hydrates, in particular, its monohydrate.

Unless specified otherwise, all technical and scientific terms used herein have the same meaning as commonly understood by one of ordinary skill in the art, to which this invention belongs. Although any methods and material or equivalent to those described herein can be used in the practice or testing of the present invention, the preferred methods and materials are described.

Further details of the process of the present invention will be apparent from the examples presented below. Examples presented are purely illustrative and are not limited to the particular embodiments illustrated herein but include the permutations, which are obvious as set forth in the description.

In the first aspect of the invention, there is provided pure l-Norepinephrine tartrate salt of Formula I having a purity by HPLC greater than 99.5% and optical purity of more than 99.5% enantiomeric excess.

In another object of the present invention, there is provided a process for the preparation of pure l-Norepinephrine tartrate salt of Formula-I having HPLC purity greater than 99.5% and optical purity more than 99.0% enantiomeric excess.

Accordingly, the process for the preparation of pure l-Norepinephrine tartrate salt of Formula-I comprising the steps of;

a) reacting catechol with chloroacetyl chloride in the presence of a Lewis acid to obtain a compound of Formula II;

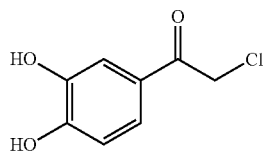

(II)

b) reacting the compound of Formula II with Hexamine to obtain compound of Formula III;

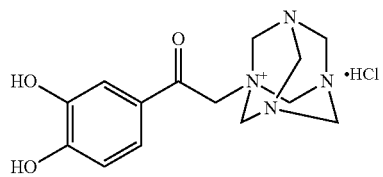

(III)

c) converting the compound of Formula III into racemic Norepinephrine HCl of formula IV;

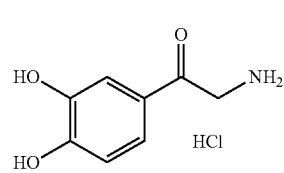

(IV)

d) hydrogenating the compound of formula (IV) to obtain dl-Norepinephrine;

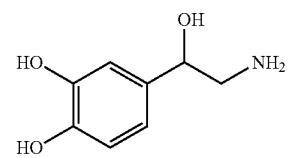

(V)

e) preparing the salt of the racemic (dl)-Norepinephrine with D-(−)-tartaric acid in water and an organic solvent at an ambient temperature to obtain crude l-Norepinephrine bitartrate;

f) converting the l-Norepinephrine bitartrate obtained in step (e) into l-Norepinephrine base by treating with a base;

g) optionally treating the l-Norepinephrine base obtained in step (f) with D-(−)-tartaric acid to obtain pure l-Norepinephrine bitartrate;

h) converting the l-Norepinephrine bitartrate in step (g) into l-Norepinephrine by treating with ammonia solution; and i) treating the l-Norepinephrine base obtained in step (h) with L-(+)-tartaric acid to obtain l-Norepinephrine Bitartrate having optical purity greater than 99% enantiomeric excess.

In another embodiment, the present invention provides process for the preparation of pure l-Norepinephrine tartrate salt of Formula-I having HPLC purity greater than 99.5% and optical purity more than 99.0% enantiomeric excess, which process comprises;

a) treating dl-Norepinephrine base with D-(−)-tartaric acid in water and an organic solvent to obtain crude l-Norepinephrine bitartrate;

b) converting the l-Norepinephrine bitartrate obtained in step (a) into l-Norepinephrine base by treating with ammonia;

c) treating the l-Norepinephrine base obtained in step (b) with D-(−)-tartaric acid to obtain pure l-Norepinephrine bitartrate;

d) converting the l-Norepinephrine bitartrate obtained in step (c) into l-Norepinephrine base by treating with ammonia; and e) treating the l-Norepinephrine base obtained in step (d) with L-(+)-tartaric acid to obtain l-Norepinephrine Bitartrate having an optical purity greater than 99% enantiomeric excess; and f) purifying the l-Norepinephrine Bitartrate monohydrate from water/IPA mixture to obtain l-Norepinephrine Bitartrate monohydrate having high optical purity of greater than 99.5%.

In yet another embodiment, the invention provides a process for the preparation of highly pure l-Norepinephrine base which process comprises;

a) treating dl-Norepinephrine base with D-(−)-tartaric acid in an aqueous alcoholic solvent to obtain crude l-Norepinephrine bitartrate;

b) converting the l-Norepinephrine bitartrate obtained in step (a) into l-Norepinephrine base by treating with ammonia;

c) optionally treating the l-Norepinephrine base obtained in step (b) with D-(−)-tartaric acid to obtain pure l-Norepinephrine bitartrate; and d) converting the l-Norepinephrine bitartrate obtained in step (c) into l-Norepinephrine base by treating with an aqueous ammonia solution.

In general, easily available any other chiral auxiliaries may be used for the resolution of the racemic Norepinephrine to (l)-Norepinephrine. The term 'chiral auxiliary' refers to enantiomerically pure organic acids having at least one chiral centre.

Examples of other chiral auxiliaries for optically resolving Norepinephrine may include D-camphor-10-sulfonic acid, L-camphor-10-sulfonic acid, D-dibenzoyltartaric acid, L-dibenzoyltartaric acid, D-mandelic acid, L-mandelic acid, and the like.

In general, the reaction of Norepinephrine free base with a chiral auxiliary may be carried out in an organic solvent. The organic solvent may include one or more solvents for example, methanol, ethanol, isopropanol, butanol, acetonitrile, dioxane, dimethylformamide, dimethylsulphoxide, halogenated solvents such as dichloromethane, chloroform and mixtures thereof. The solvent mixture also includes aqueous organic solvent mixtures. The reaction of Norepinephrine free base with a chiral auxiliary in an organic solvent may result in the formation of two diastereomeric salts of Norepinephrine. The separation of the diastereomeric salt from the reaction mixture may be carried out by filtration. Desired isomer may be converted into a free base by treating the separated diastereomeric salt with a basifying agent. The steps of formation of the diastereomeric salt, separation of the desired salt and subsequent conversion of the salt to the free base can be repeated to enrich the optical purity of (l)-Norepinephrine free base.

For clinical use, the optically pure compounds of the invention are formulated into pharmaceutical compositions for injection. The optically pure compounds of the invention can be used, either individually or in combination with other active agents. The optically pure compounds of the invention can be used in treatment of restoration of blood pressure in hypotensive states and also as an adjunct in treatment of Cardiac arrest. The pharmaceutical composition contains the optically pure compounds of the invention normally in combination with a pharmaceutically acceptable carrier like purified water or water for injection. The carrier may be in form of a liquid diluent. The amount of active compound is between 0.1-95 percent by weight of the pharmaceutical composition, preferably, between 0.01-25 percent by weight in pharmaceutical composition for parenteral use.

Solutions for parenteral (Injectable) administrations may be prepared as solutions of the optically pure compounds of the invention in pharmaceutically acceptable solvents like water for injection and/or alcohol, preferably in a concentration from 0.1 to 20% by weight. These solutions may also contain, tonicity adjuster (e.g. sodium chloride), preservatives (e.g. methyl paraben), antioxidants (e.g. sodium metabisulfite), stabilizing agents (e.g. edetate disodium or citric acid anhydrous), pH adjustor (sodium hydroxide or hydrochloric acid), and buffering agents (e.g. sodium lactate) and may be manufactured in different unit dose ampoules or vials. Preferably, the optically pure compound of the invention can be dispensed in concentration of 1 mg/ml for intravenous administration after appropriate dilution.

In general, dose/infusion rate for optically pure compounds of the invention varies from 0.4 mg/hour to 0.8 mg/hour Norepinephrine base which is equivalent to the infusion rate of 0.8 mg/hour to 1.6 mg/hour of norepinephrine tartrate.

The methods of manufacturing of Norepinephrine injection are well known to the person skilled in the art.

Following examples are provided to further illustrate the present invention but in no way limit the scope of the present invention.

Reference Example-1 (U.S. Pat. No. 2,774,789, Example-A)

Preparation of l-Norepinephrine Bitartrate

To a four necked 100 ml flask charged racemic Norepinephrine base (20 gm), d-(−) tartaric acid (18.34 gm), and water (35 ml) at room temperature. The reaction mass was stirred to obtain clear solution, cooled to 0-5° C. After 5 hours slight turbidity was observed. Turbidity increases slowly to get thick white slurry after 6 hours, reaction mass becomes very thick which was difficult to filter, washed solid wet cake by 4.0 ml water followed by two 12 ml portions of 95% ethanol. Suck dried the solid completely, dried at 45° C. to get l-Norepinephrine Bitartrate (28 gm) which is in crude form.

Crude l-Norepinephrine Bitartrate (20 gm) dissolved in 14 ml of water at 50° C. Clear solution was obtained. Activated charcoal was added to this solution and stirred the reaction mass for more than 30 min. Filtered through Hyflo and cooled to 0-5° C. After 2 hours, clear solution obtained gets converted to thick solid mass. Filtered and washed the solid with 1.5 ml of chilled water followed 14 ml of 95% ethanol.

This dry solid 8 gm (after $1^{st}$ purification) was then dissolved in 8 ml of water at 50° C. to get clear solution. This reaction mass was then cooled to 0-5° C. After 1 hour, a clear solution gets converted to a thick solid mass. Maintained the reaction mass for more than 2 hours at the same conditions. Filtered the thick solid and washed with 95% ethanol. Dried the solid at 45° C. to obtain l-Norepinephrine Bitartrate.

Chiral Purity by HPLC: l-Norepinephrine Bitartrate=68.45%, and d-isomer=31.55%

Specific Optical Rotation: −6.33°

Reference Example-2 (JAGS, 1948, Page-2067-68, Example-a)

To a four necked flask charged racemic Norepinephrine base (20 gm), d-(−) tartaric acid (18.34 gm), and water (35.20 ml) at room temperature. After 5 minutes reaction mass becomes clear liquid. Cooled the reaction mass to 2-3° C. After 30 minutes, reaction mass was observed to be turbid and further the reaction mass becomes very thick. This mass was, stirred for 2 hours at 0-5° C. Then filtered reaction mass at same temperature and washed solid wet cake with 3.5 ml water followed by two 11.8 ml portions of 95% ethanol. Dried the solid at air oven at 45° C. to get crude tartrate salt (15 gm).

Crude tartrate salt (15 gm) was dissolved in 5 ml of water at 50° C. to get clear solution. Cooled to 2-3° C. After 30 minutes, a clear solution gets converted to a thick solid mass. Filtered the solid and washed with 1.5 ml of chilled water and then 15 ml of 95% ethanol. Dried the solid at 45° C. to obtain semi pure l-Norepinephrine Bitartrate (8 gm).

This semi pure l-Norepinephrine Bitartrate (8 gm) was dissolved in 8 ml of water at 50° C. to get clear solution. Cooled the mass to 2-3° C. After 30 minutes clear solution gets converted to thick solid mass. Filtered the solid and washed with 8 ml of 95% ethanol. Dried the solid at 45° C. to obtain pure l-Norepinephrine Bitartrate (3 gm).

Chiral Purity: l-Norepinephrine Bitartrate=77.14%, d-isomer=22.86%

Specific Optical Rotation: −10.4°

Example-1: Preparation of 2-Chloro-1-(3, 4-Dihydroxyacetophenone)

In round bottom flask, charged Methylene Chloride (1000 ml), Aluminium chloride (300 gm) and cooled to 0-5° C. Pyrocatechol (100 gm) was added lot wise. Chloroacetyl chloride (108 gm) was added drop wise at 0-5° C. Then stirred the reaction mass at 25-30° C. for 20-24 hours. After completion of the reaction, reaction mass was quenched in aq. HCl, filtered the reaction mass and wet cake was charged in water containing acetic acid. Filtered the reaction mass and cooled to 15-20° C., filtered solid and washed with water.

Yield: 110 gm.
HPLC Purity: 99.5%

Example-2: Preparation of Hexamine Salt

In a round bottom flask charged 2-chloro-1-(3, 4-dihydroxyacetophenone) (100 gm), Hexamine (87 gm), IPA (500 ml), Chloroform (400 ml). Stirred the reaction mass at reflux temperature for 6 hours. After completion of the reaction, cooled to 25-30° C., filtered and washed the wet cake with IPA and Methanol.

Yield: 160 gm.
HPLC Purity: 99.3%

Example-3: Preparation of 2-Amino-1-(3,4-Dihydroxyphenyl)Ethanone Hydrochloride In a round bottom flask charged Hexamine salt (100 gm), Methanol (600 ml), aqueous HCl and heated the reaction mass to 55-60° C. After completion of the reaction, the mass was dissolved in water, by adjusting pH with liquor ammonia. Filtered the solid and washed with water, dried the material at 45-50° C.

This free base was charged in 900 ml methanol and pH was adjusted to 1-1.5 by IPA.HCl and distilled off methanol completely to get white solid which was isolated by filtration.

Yield: 37 gm
HPLC Purity: 99.5%

Example-4: Preparation of [4-(2-Amino-1-Hydroxyethyl) Benzene-1, 2-Diol] (Racemic Norepinephrine Base)

Charged 2-amino-1-(3, 4-dihydroxyphenyl) ethanone hydrochloride (100 gm), 10% Pd/C(10 gm), methanol (700 ml) and water (300 ml) mixture in autoclave. Stirred the reaction mass at 40-45° C. After completion of reaction, Pd/C was removed by filtration. Collected filtrate and distilled off methanol. pH was adjusted by liquor ammonia. Isolated the solid by filtration and washed with water followed by methanol. Dried the solid at 40-45° C.

Yield: 67 gm
Purity: 99.2%

Example-5: Preparation of l-Norepinephrine Base

Charged racemic Norepinephrine base (100 gm), D-(−)-Tartaric acid (142 gm), water (100 ml) in a round bottom flask. The reaction mass was stirred to get clear solution. After some time, solid started to crystallize. Reaction mass was diluted with methanol (900 ml). Maintained the reaction mass under stirring for 24 hours at 25-30° C. Filtered and washed the wet cake with methanol to obtain Crude l-Norepinephrine tartrate salt.

Yield: 85 gm

The crude l-Norepinephrine tartrate salt was converted into its free base by dissolving this crude tartrate salt in water (500 ml) and adjusted pH to 8-8.5 by liquor ammonia and isolated the solid by filtration. Dried the material at 40-45° C. to obtain pure l-Norepinephrine free base (43 gm).

Yield: 43 gm (l-Norepinephrine pure base).
HPLC Purity: 99.7%
Chiral Purity: 98.0%

Example-6: Preparation of Pure l-Norepinephrine Base

Charged l-Norepinephrine base (100 gm) obtained from Example-5, D-(−)-Tartaric acid (142 gm), water (100 ml) in a round bottom flask. The reaction mass was stirred to get clear solution. After some time, a solid started to crystallize. Reaction mass was diluted with methanol (900 ml). Maintained the reaction mass under stirring for 24 hours at 25-30° C. Filtered and washed the wet cake with methanol to obtain l-Norepinephrine tartrate salt.

Yield: 88 gm

The l-Norepinephrine tartrate salt was converted into its free base by dissolving this crude tartrate salt in water (500 ml) and adjusted the pH to 8-8.5 by liquor ammonia and isolated the solid by filtration. Dried the material at 40-45° C. to obtain pure l-Norepinephrine free base (44 gm).

Yield: 44 gm (l-Norepinephrine pure base).
HPLC Purity: 99.7%
Chiral Purity: 99.1%

Example-7: Preparation of Highly Pure Norepinephrine Bitartrate Monohydrate

Charged Norepinephrine pure base (100 gm), L-(+) tartaric acid (100 gm), water (100 ml) and methanol (900 ml), Stirred the reaction mass to get clear solution. After some time, a solid started to crystallize then the reaction mass was diluted with methanol (900 ml). Maintained the reaction mass under stirring at 25-30° C. for 24 hours. Filtered and washed the wet cake with methanol to obtain Norepinephrine Bitartrate Monohydrate (90 gm).

HPLC Purity: 99.8%
Chiral Purity: 99.4%

Example-8: Purification of l-Norepinephrine Bitartrate Monohydrate

Charged 100 gm tartrate salt obtained from example-6, purified water (100 ml) and heated the reaction mass to 40-45° C. to obtain clear solution, cooled to 0-5° C. Charged IPA (100 ml) slowly and the mass was stirred for one hour. The solid was isolated by filtration and washed with IPA. Dried the material at 40-45° C. to obtain l-Norepinephrine Bitartrate Monohydrate (82 gm) having high enantiomeric purity.
HPLC Purity: 99.85%
Chiral Purity: 99.87%
Specific Optical rotation: −11.0°

Example-9

The following table sets forth the high purity of the l-Norepinephrine Bitartrate monohydrate of the invention as compared with prior art references.

| Purity Criteria | U.S. Pat. No. 2,774,789 Example-A | Reference Example-2 (JACS, 1948, Page-2067-68, Example-a) | l-Norepinephrine Bitartrate monohydrate of the present invention |
|---|---|---|---|
| Optical purity of l-Norepinephrine Bitartrate monohydrate | 68.45% | 77.14% | 99.87% |
| Specific Optical rotation (Limit: −10° to −12°) | −6.33° | −10.4° | −11.0° |

It is evident from the above table that the compound of the present invention has substantially improved optical purity.

What is claimed is:

1. A process for the preparation of optically pure l-Norepinephrine bitartrate monohydrate, wherein the process comprises;
   a) treating dl-Norepinephrine base with D-(−)-tartaric acid in the presence of water and an organic solvent to obtain crude l-Norepinephrine bitartrate;
   b) converting the l-Norepinephrine bitartrate obtained in step (a) into l-Norepinephrine base;
   c) treating the l-Norepinephrine base obtained in step (b) with L-(+)-tartaric acid and water to obtain l-Norepinephrine Bitartrate monohydrate having an optical purity of greater than 99%.

2. The process as claimed in claim 1, wherein step (b) comprises converting the l-Norepinephrine bitartrate obtained in step (a) into l-Norepinephrine base by treating with ammonia.

3. The process as claimed in claim 1, wherein step (b) comprises:
   a first step of converting the l-Norepinephrine bitartrate obtained in step (a) into l-Norepinephrine base by treating with ammonia;
   a second step of treating the l-Norepinephrine base obtained in the first step with D-(−)-tartaric acid to obtain pure l-Norepinephrine bitartrate; and
   a third step of converting the l-Norepinephrine bitartrate obtained in the second step into l-Norepinephrine base by treating with aqueous ammonia solution.

4. The process as claimed in claim 1, further comprising:
   d) purifying the l-Norepinephrine Bitartrate monohydrate obtained in step (c) from a water/IPA mixture to obtain l-Norepinephrine Bitartrate monohydrate having an optical purity of greater than 99.5%.

5. The process as claimed in claim 1, wherein the organic solvent is selected from the group consisting of methanol, ethanol, isopropanol, n-butanol, acetonitrile, dioxane, dimethylformamide, dimethylsulphoxide, halogenated solvents, and mixtures thereof.

6. The process as claimed in claim 1, wherein the organic solvent is a halogenated solvent selected from the group consisting of dichloromethane, chloroform, and mixtures thereof.

7. The process as claimed in claim 1, further comprising, prior to step (a), a step of preparing the dl-Norepinephrine base by:
   a) reacting catechol with chloroacetyl chloride in the presence of a Lewis acid to obtain a compound of Formula II;

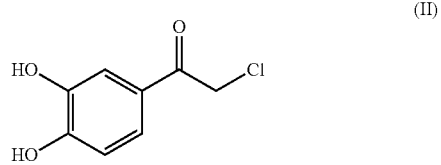 [SMILES: O=C(CCl)c1ccc(O)c(O)c1]

b) reacting the compound of Formula II with Hexamine;
   c) converting the product of step (b) into the hydrochloride salt of a ketone of formula IV; and

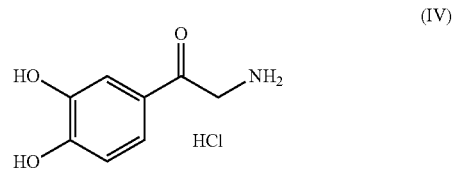 [SMILES: NCC(=O)c1ccc(O)c(O)c1 ; Cl]

d) hydrogenating the ketone of formula (IV) to obtain dl-Norepinephrine of formula V;

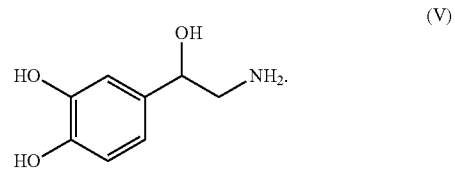 [SMILES: NCC(O)c1ccc(O)c(O)c1]

8. A pharmaceutical composition comprising:
   l-Norepinephrine bitartrate monohydrate having an optical purity of more than 99.5%, prepared by the method of claim 1; and
   one or more pharmaceutically acceptable carrier(s).

9. A process for the preparation of optically pure l-Norepinephrine bitartrate monohydrate, wherein the process comprises;

a) treating dl-Norepinephrine base with D-(−)-tartaric acid in the presence of water and an organic solvent to obtain crude l-Norepinephrine bitartrate;
b) converting the l-Norepinephrine bitartrate obtained in step (a) into l-Norepinephrine base by performing:
   a first step of converting the l-Norepinephrine bitartrate obtained in step (a) into l-Norepinephrine base;
   a second step of treating the l-Norepinephrine base obtained in the first step with D-(−)-tartaric acid to obtain pure l-Norepinephrine bitartrate; and
   a third step of converting the l-Norepinephrine bitartrate obtained in the second step into l-Norepinephrine base by treating with aqueous ammonia; and
c) treating the l-Norepinephrine base obtained in the third step with L-(+)-tartaric acid and water to obtain l-Norepinephrine Bitartrate monohydrate having an optical purity of greater than 99%.

\* \* \* \* \*